(12) United States Patent
Hyde et al.

(10) Patent No.: US 8,639,347 B2
(45) Date of Patent: Jan. 28, 2014

(54) METHODS, DEVICES AND SYSTEMS FOR TRANSMISSION BETWEEN AN IMPLANTED DEVICE AND AN EXTERNAL DEVICE

(75) Inventors: Roderick A. Hyde, Redmond, CA (US); Muriel Y. Ishikawa, Livermore, CA (US); Jordin T. Kare, Seattle, WA (US); Dennis J. Rivet, Portsmouth, VA (US); Lowell L. Wood, Jr., Bellevue, WA (US); Victoria Y. H. Wood, Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 547 days.

(21) Appl. No.: 12/658,627

(22) Filed: Feb. 9, 2010

(65) Prior Publication Data
US 2010/0295372 A1     Nov. 25, 2010

Related U.S. Application Data

(63) Continuation-in-part of application No. 12/283,911, filed on Sep. 15, 2008, now Pat. No. 8,340,777, and a continuation-in-part of application No. 12/316,811, filed on Dec. 15, 2008, now Pat. No. 8,280,520, and a continuation-in-part of application No. 12/378,152, filed on Feb. 11, 2009, now Pat. No. 8,295,941, and a continuation-in-part of application No. 12/456,846, filed on Jun. 23, 2009, now Pat. No. 8,463,391.

(51) Int. Cl.
*A61N 1/00* (2006.01)

(52) U.S. Cl.
USPC .......................................................... 607/60

(58) Field of Classification Search
USPC .......................................................... 607/60
See application file for complete search history.

(56) References Cited

U.S. PATENT DOCUMENTS

| 5,320,098 A | 6/1994 | Davidson |
| 5,387,259 A | 2/1995 | Davidson |
| 5,835,457 A | 11/1998 | Nakajima |
| 5,889,735 A | 3/1999 | Kawata et al. |
| 5,897,330 A | 4/1999 | Watanabe et al. |
| 6,898,464 B2 | 5/2005 | Edell et al. |
| 2006/0139000 A1 | 6/2006 | Bailey et al. |
| 2007/0027505 A1 | 2/2007 | Ginggen |
| 2008/0097545 A1 * | 4/2008 | Propato ........................ 607/32 |
| 2009/0171404 A1 * | 7/2009 | Irani et al. ..................... 607/2 |

OTHER PUBLICATIONS

U.S. Appl. No. 12/456,846, filed Jun. 23, 2009, Hyde et al.
U.S. Appl. No. 12/283,911, filed Sep. 15, 2008, Hyde et al.
U.S. Appl. No. 12/316,811, filed Dec. 15, 2008, Hyde et al.
U.S. Appl. No. 12/378,152, filed Feb. 11, 2009, Hyde et al.
U.S. Appl. No. 13/604,005, filed Oct. 29, 2012, Hyde et al.
U.S. Appl. No. 13/603,904, filed Oct. 29, 2012, Hyde et al.
U.S. Appl. No. 13/603,859, filed Oct. 29, 2012, Hyde et al.

* cited by examiner

*Primary Examiner* — Eric D. Bertram
(74) *Attorney, Agent, or Firm* — Dorsey & Whitney LLP

(57) ABSTRACT

Embodiments disclosed herein are directed to systems including an internal power transmitter that delivers energy out of a living subject to power at least one external device that is in communication with the internal power transmitter, and related apparatuses, devices, and methods of use.

33 Claims, 11 Drawing Sheets

METHODS, DEVICES AND SYSTEMS FOR TRANSMISSION BETWEEN AN IMPLANTED DEVICE AND AN EXTERNAL DEVICE

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation-in-part of U.S. patent application Ser. No. 12/283,911, entitled SYSTEMS CONFIGURED TO TRANSMIT OPTICAL POWER SIGNALS TRANSDERMALLY OUT OF A LIVING SUBJECT, AND DEVICES AND METHODS, naming RODERICK A. HYDE, MURIEL Y. ISHIKAWA, DENNIS J. RIVET, ELIZABETH A. SWEENEY, LOWELL L. WOOD, JR., AND VICTORIA Y. H. WOOD as inventors, filed 15 SEPT. 2008, which is now U.S. Pat. No. 8,340,777, or is an application of which a currently co-pending application is entitled to the benefit of the filing date.

For purposes of the USPTO extra-statutory requirements, the present application constitutes a continuation-in-part of U.S. patent application Ser. No. 12/316,811, entitled SYSTEMS CONFIGURED TO LOCATE A PHOTONIC DEVICE DISPOSED IN A LIVING SUBJECT, AND RELATED APPARATUSES AND METHODS, naming RODERICK A. HYDE, MURIEL Y. ISHIKAWA, DENNIS J. RIVET, LOWELL L. WOOD, JR., AND VICTORIA Y. H. WOOD as inventors, filed 15 Dec. 2008, which is now U.S. Pat. No. 8,280,520, or is an application of which a currently co-pending application is entitled to the benefit of the filing date.

For purposes of the USPTO extra-statutory requirements, the present application constitutes a continuation-in-part of U.S. patent application Ser. No. 12/378,152, entitled SYSTEMS CONFIGURED TO POWER AT LEAST ONE DEVICE DISPOSED IN A LIVING SUBJECT, AND RELATED APPARATUSES AND METHODS, naming RODERICK A. HYDE, MURIEL Y. ISHIKAWA, DENNIS J. RIVET, LOWELL L. WOOD, JR., AND VICTORIA Y. H. WOOD as inventors, filed 11 Feb. 2009, which is now U.S. Pat. No. 8,295,941, or is an application of which a currently co-pending application is entitled to the benefit of the filing date.

For purposes of the USPTO extra-statutory requirements, the present application constitutes a continuation-in-part of U.S. patent application Ser. No. 12/456,846, entitled SYSTEMS CONFIGURED TO DELIVER ENERGY OUT OF A LIVING SUBJECT, AND RELATED APPARATUSES AND METHODS, naming RODERICK A. HYDE, MURIEL Y. ISHIKAWA, DENNIS J. RIVET, LOWELL L. WOOD, JR., AND VICTORIA Y. H. WOOD as inventors, filed 23 Jun. 2009, which is now U.S. Pat. No. 8,463,391, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

SUMMARY

In an embodiment, a system includes an internal power transmitter configured to be disposed within a living subject. The internal power transmitter is further configured to deliver energy out of the living subject. The system can further include an internal receiver configured to be disposed within the living subject. The internal receiver is further configured to receive and process a request for action from an external device located external to the living subject.

In an embodiment, a method includes transmitting a request for information, about one or more operational characteristics of an internal power transmitter, to receiver. At least the internal power transmitter is disposed within a living subject. The method additionally includes receiving one or more signals delivered out of the living subject from the internal power transmitter in response to the transmitting the request. The one or more signals can encode information about the one or more operational characteristics of the internal power transmitter. The method further includes receiving power, at an external device located external to the living subject, which is delivered from the internal power transmitter out of the living subject.

In an embodiment, a method includes transmitting a request to a receiver to receive power from an internal power transmitter. At least the internal power transmitter is disposed within a living subject. The method further includes receiving power, at an external device located external to the living subject, which is delivered from the internal power transmitter out of the living subject.

In an embodiment, a method includes receiving a request for information about an internal power transmitter at a receiver associated with the internal power transmitter. At least the internal power transmitter is disposed within a living subject. The method further includes delivering the information out of the living subject to an external device.

In an embodiment, a method includes receiving a request for information about an internal power transmitter at a receiver associated with the internal power transmitter. At least the internal power transmitter is disposed within a living subject. The method further includes delivering the information to an external device that is disposed external to the living subject.

In an embodiment, an apparatus configured for disposal in a living subject includes an internal power transmitter, an internal receiver, and a biocompatible protective packaging. The internal power transmitter is configured to deliver energy out of the living subject. The internal receiver is configured to receive and process a request for action from an external device located external to the living subject. The biocompatible protective packaging at least partially encloses the internal power transmitter and the internal receiver.

In an embodiment, a device includes a power receiver, electrical circuitry, a transmitter, and a location-identifying device. The power receiver is configured to receive power delivered out of a living subject. The electrical circuitry is operably coupled to the power receiver to receive energy at least associated with the power. The transmitter configured to deliver a request for action to an internal receiver disposed in the living subject. The location-identifying device configured coordinate a location thereof with respect to an internal power transmitter disposed in the living subject.

The foregoing is a summary and thus may contain simplifications, generalizations, inclusions, and/or omissions of detail; consequently, the reader will appreciate that the summary is illustrative only and is NOT intended to be in any way limiting. Other aspects, features, and advantages of the devices and/or processes and/or other subject matter described herein will become apparent after reading the teachings set forth herein.

DETAILED DESCRIPTION

Figure 1A:
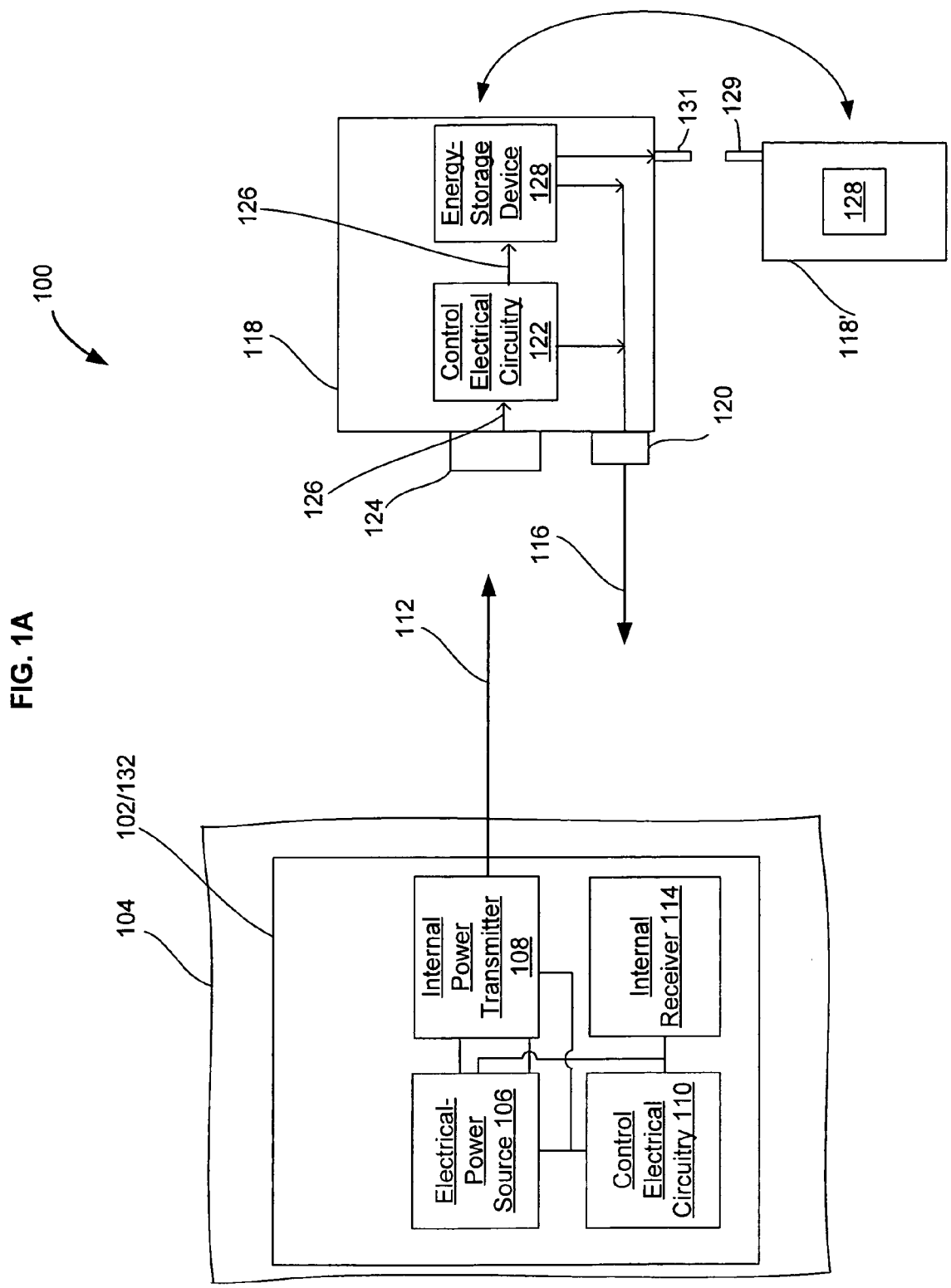
FIG. 1A is a functional block diagram of an embodiment of a system including an internal power transmitter that delivers energy out of a living subject to power at least one external device that is in communication with the internal power transmitter.

Embodiments disclosed herein are directed to systems including an internal power transmitter that delivers energy out of a living subject to power at least one external device that is in communication with the internal power transmitter, and related apparatuses, devices, and methods of use. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein.

FIG. 1A is a functional block diagram of an embodiment of a system 100 including an internal power transmitter that delivers energy out of a living subject to power at least one external device that is in communication with the internal power transmitter. The system 100 includes an apparatus 102 configured to be disposed within a living subject 104, such as being embedded in tissue, muscle, or bone of a human being. For example, the apparatus 102 may be configured to be disposed subdermally. The apparatus 102 includes an electrical-power source 106, an internal power transmitter 108 coupled to the electrical-power source 106 to receive electrical power (e.g., one or more electrical signals) therefrom, and control electrical circuitry 110 configured to control distribution of the electrical power from the electrical-power source 106 to the internal power transmitter 108 and the operation of the internal power transmitter 108. The internal power transmitter 108 is configured to convert at least a portion of the electrical power received from the electrical-power source 106 into a different type of energy 112 and deliver the energy 112 out of the living subject 104 at a power of, for example, at least about 10 µW. In an embodiment, the energy 112 may be delivered transdermally through and out of tissue of the living subject 104.

The apparatus 102 further includes an internal receiver 114 configured to receive and process one or more signals 116 encoding a request for action received from at least one external device 118, and communicate the request for action to the control electrical circuitry 110 that, in turn, instructs the internal power transmitter 108 about how to operate in accordance with the received request for action. For example, the internal receiver 114 may communicate the request to the control electrical circuitry 110, which in turn instructs the internal power transmitter 108, via a wired or wireless connection (e.g., ultrasonic signals, radio-frequency signals, electromagnetic signals, or optical signals). The internal receiver 114 may be powered by the electrical-power source 106 or another, separate, dedicated electrical-power source. The internal receiver 114 may be controlled by the control electrical circuitry 110 or another, separate, dedicated control electrical circuitry. The internal receiver 114 may be configured as an optical receiver (e.g., one or more photodiodes), a radio-frequency receiver, an ultrasonic transducer, an electromagnetic receiver, or another suitable type of receiver. In an embodiment, the internal power transmitter 108 and the internal receiver 114 may be combined to form an integrated transceiver.

In an embodiment, the request for action, encoded in the one or more signals 116, may include a request for information about one or more operational characteristics of the internal power transmitter 108, such as power level of the energy 112, frequency of the energy 112, pulse duration of the energy 112, time profile of the energy 112, type of the energy 112, delivery characteristics of the energy, price of the energy 112, amount of available energy 112 that the internal power transmitter 108 is capable of delivering, location of the internal power transmitter 108, or other selected operational characteristic. In an embodiment, the request for action, encoded in the one or more signals 116, may include a request or an authorization for the internal power transmitter 108 to deliver the energy 112 or to stop delivering the energy 112. For example, when the request for action includes an authorization for the internal power transmitter 108 to deliver the energy 112 or to stop delivering the energy 112, the request for action may include authorization data. In an embodiment, the request for action includes a request for the energy 112 at a selected power level, a request for the energy 112 with a selected time profile, a request for a selected amount of the energy 112, or a request for the energy 112 at a specific price.

The external device 118 is positioned or positionable externally to the living subject 104 to receive the converted energy 112 transmitted out of the living subject 104. For example, the external device 118 may be configured as an electronic device, such as a cell phone, a camera, a personal data assistant, a video game device, a therapeutic device, a sensor, or an electronic medical device (e.g., a hearing aid). The external device 118 includes an external transmitter 120 configured to transmit the one or more signals 116 to the internal receiver 114 that encode the request for action. The one or more signals 116 may have a peak wavelength that is transdermally transmittable through the tissue of the living subject 104. For example, the one or more signals 116 may include one or more optical data signals (e.g., one or more infrared or ultraviolet peak optical data signals), one or more radio-frequency data signals, one or more ultrasonic data signals, or one or more electromagnetic signals encoding the request for action that are at least partially transmittable through the tissue of the living subject 104. The external device 118 further includes control electrical circuitry 122 configured to control the operation of the external transmitter 120.

The external device 118 further includes a converter 124 (i.e., a power receiver) that is configured to convert the received energy 112 output by the internal power transmitter 108 into electrical power 126. For example, the converter 124 may be integrated with or separate from the external device 118. The external device 118 may further include an energy-storage device 128 (e.g., a capacitive device or a battery) configured to store the converted electrical power 126 received from the control electrically circuitry 122 for powering the external device 118. The control electrical circuitry 122 may be coupled to the energy-storage device 128 and configured to control the distribution of electrical power 126 to the energy-storage device 128 and the operation of the external device 118. In an embodiment, the energy-storage device 128 may be configured as a re-chargeable removable battery that may be removed from the external device 118 and installed in another external device 118' to serve as its power source. The external device 118' may be selected from any of the devices that the external device 118 may be selected from.

As an alternative to swapping the energy-storage device 128, the external device 118' may be provided with a power interface 129, such as an inductive receiver, an electrical receiver (e.g., electrical socket), or other suitable interface configured to receive power from the external device 118. In such an embodiment, the external device 118 may be provided with a power interface 131 configured to transmit power from the energy-storage device 128 to another energy-storage device in the external device 118'. For example, the power interface 131 may be an inductive transmitter that inductively couples power to the power interface 129 when it is configured as an inductive receiver, an electrical plug that electrically couples to the power interface 129 when it is an electrical socket, or other suitable power interface configured to transfer power from the energy-storage device 128 and to another energy-storage device into the external device 118'.

The electrical-power source 106, internal power transmitter 108, control electrical circuitry 110, and internal receiver 114 may be configured to be disposed in the living subject 104, such as by being sized for being disposed in the living subject 104 or being biocompatible with the living subject 104. For example, the electrical-power source 106, internal power transmitter 108, control electrical circuitry 110, and internal receiver 114 may be compactly enclosed in a biocompatible protective packaging 132 that is disposed within the living subject 104 to form the apparatus 102. In an embodiment, the electrical-power source 106, internal power transmitter 108, control electrical circuitry 110, and internal receiver 114 may each be individually enclosed in separate biocompatible protective packaging sections.

In operation, the transmitter 120 of the external device 118 outputs the one or more signals 116 encoding the request for action, which are received by the internal receiver 114 disposed in the living subject 104. In the illustrated embodiment, the one or more signals 116 are one or more optical, radio-frequency, ultrasonic, or electromagnetic signals transmitted transdermally through the tissue of the living subject. The internal receiver 114 transmits the request for action to the internal power transmitter 108. The electrical-power source 106 provides the internal power transmitter 108 with the electrical power, and the internal power transmitter 108 converts at least a portion of the electrical power into the energy 112. In accordance with the received request for action, the operation of the internal power transmitter 108 is controlled. In an embodiment, the internal power transmitter 108 may transmit the energy 112 to the external device 118 encoding information about one or more operational characteristics of the internal power transmitter 108 when requested by the external device 118 in the request for action. In an alternative embodiment, the apparatus 102 may include a separate transmitter or a transmitter integrated with the internal receiver 114 that forms a transceiver, which is coupled to the control electrical circuitry 110 that transmits energy transmdermally out of the living subject 104 encoding the information about the one or more operational characteristics of the internal power transmitter 108. For example, the external device 118 may alter one or more operational characteristics so that it is capable of better receiving power from the internal power transmitter 108, such as altering an orientation of the converter 118 or other selected operational characteristic.

After, or in lieu of, the internal power transmitter 108 sending the external device 118 information, in an embodiment, the internal power transmitter 108 transmits the energy 112 out of the living subject 104 with, for example, a power of at least about 10 µW to power the external device 118. More specifically, the internal power transmitter 108 transmits the energy 112 transdermally through and out of the living subject 104 in response to instructions from the control electrical circuitry 110 and the received request for action from the external device 118. The energy 112 may be received by the converter 124 of the external device 118, which converts the received energy 112 to the electrical power 126. The electrical power 126 is transmitted to the control electrical circuitry 122, which distributes the electrical power 126 to the energy-storage device 128 for storage and use as power to power the external device 118.

In an embodiment, the converter 124 of the external device 118 may be placed in proximity to the internal power transmitter 108 and abut tissue of the living subject 104. In an embodiment, the energy 112 may be output from the internal power transmitter 108 and transmitted transdermally out of the living subject 104 with a power that is sufficient so that the external device 118 may be positioned remote from the living subject 104 and the internal power transmitter 108 disposed therein.

Figure 1B:
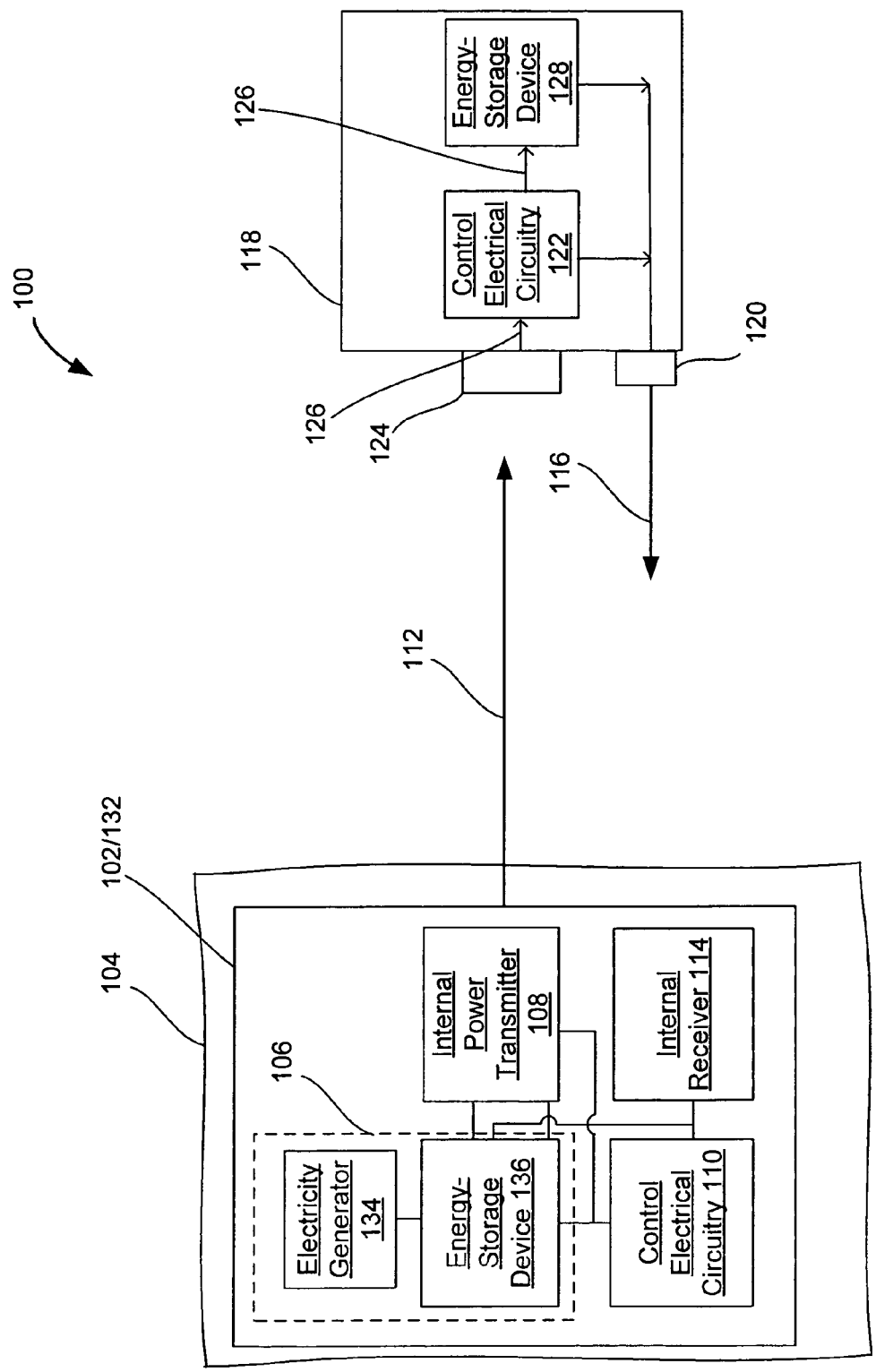
FIG. 1B is a functional block diagram of an embodiment of the system shown in FIG. 1A in which the electrical-power source includes an energy-storage device that stores energy generated by an electricity generator configured to convert internal body energy of the living subject to electrical energy.

The internal power transmitter 108 may receive power from a variety of different types of power sources. According to one or more embodiments, the electrical-power source 106 may include an energy storage device, such as a battery or a capacitive device. Referring to FIG. 1B, in an embodiment, the electrical-power source 106 may include an electricity generator 134 configured to convert internal body energy of the living subject 104 to electrical energy. For example, the electricity generator 134 may include at least one of a fluid-flow generator configured to convert internal body fluid motion into electricity, a fluid-pressure generator configured to convert internal fluid pressure into electricity, a muscle-motion generator configured to convert internal muscle motion into electricity, an acceleration-motion generator configured to convert acceleration of the living subject 104 into electricity, or a thermal-electric generator configured to convert internal body heat into electricity. The electrical-power source 106 may further include an energy-storage device 136 (e.g., a battery or capacitive device) coupled to the electricity generator 134 and configured to store electrical energy generated thereby. In such an embodiment, the control electrical circuitry 110 may be coupled to the energy-storage device 136 and control distribution of the electricity therefrom to the internal power transmitter 108. In an embodiment, the electricity generator 134 may be omitted, and the energy-storage device 136 may be a disposable or re-chargeable battery that powers the internal power transmitter 108. In an embodiment, the energy-storage device 136 and the electricity generator 134 may be separately packaged in a biocompatible packaging.

The internal power transmitter 108 may be configured to deliver the energy 112 out of the living subject 104 with, for example, a power of at least about 10 µW. In more specific embodiments, the power output by the internal power transmitter 108 may range from about 10 µW to about 10 W, about 10 µW to about 1 mW, about 1 mW to about 100 W, about 100 mW to about 1 W, about 1 W to about 5 W, about 5 W to about 10 W, about 10 µW to about 100 W, about 1 W to about 100 W, or about 20 W to about 100 W. The internal power transmitter 108 may output the energy 112 at a selected one or more wavelengths that are transmittable through the tissue of the living subject 104. For example, the selected one or more wavelengths may include one or more infrared wavelengths having a wavelength of about 800 nm to about 1 mm. The selected one or more wavelengths may also include one or more visible wavelengths having a wavelength of about 380 nm to about 750 nm.

The internal power transmitter 108 may be chosen from a number of different types of transducers that are configured to convert electrical energy to another form of energy. In an embodiment, the transducer may include an electrical-optical converter configured to convert at least a portion of the electrical power received from the electrical-power source 106, and deliver the converted electrical power as the energy 112 in the form of electromagnetic energy such as one or more optical power signals. For example, the electrical-optical converter may be a light-emitting device, such as one or more light-emitting diodes or one or more laser diodes. In such an embodiment, the converter 124 of the external device 118 may be an optical-electrical converter (e.g., one or more photodiodes) configured to convert the received energy 114 to the electrical power 120. In an embodiment, when the internal power transmitter 108 delivers one or more signals encoding information about the internal power transmitter 108, the internal power transmitter 108 may be a wavelength or power tunable light-emitting device (e.g., a light-emitting diode) so that the wavelength or power of the energy 112 may be controlled.

In an embodiment, the transducer may include an electrical-magnetic converter configured to convert at least a portion of the electrical power received from the electrical-power source 106, and output the converted electrical power as the energy 112 in the form of magnetic energy. For example, the electrical-magnetic converter may be an electromagnet. In such an embodiment, the converter 124 of the external device 118 may be a magnetic-electrical converter (e.g., induction coil) configured to convert the received energy 112 to the electrical power 126.

In an embodiment, the transducer may include one or more ultrasonic elements configured to convert at least a portion of the electrical power received from the electrical-power source 106, and output the converted electrical power as the energy 112 in the form of ultrasonic energy. For example, the one or more ultrasonic elements may be one or more piezoelectric elements. In such an embodiment, the converter 124 of the external device 118 may also include one or more ultrasonic elements configured to convert the received ultrasonic energy to the electrical power 126.

In an embodiment, the transducer may include a heating element configured to convert at least a portion of the electrical power received from the electrical-power source 106 to the energy 112 in the form of thermal energy. For example, the heating element may be one or more resistance heating elements. In such an embodiment, the converter 124 of the external device 118 may also include a thermal-electric converter (e.g., one or more Peltier cells or an alkali metal thermal-electric converter) configured to convert the received ultrasonic energy to the electrical power 126.

In an embodiment, the transducer may include a radio-frequency device configured to convert at least a portion of the electrical power received from the electrical-power source 106 to the energy 112 in the form of radio-frequency energy. For example, the radio-frequency device may be a radio-frequency transmitter. In such an embodiment, the converter 124 of the external device 118 may include a radio-frequency receiver configured to convert the received radio-frequency energy to the electrical power 126.

In an embodiment, the transducer may include a device configured to convert at least a portion of the electrical power received from the electrical-power source 106 to the energy 112 in the form of electromagnetic energy. In such an embodiment, the converter 124 of the external device 118 may include electromagnetic-electrical configured to convert the received electromagnetic energy to the electrical power 126.

As previously discussed, the electrical-power source 106 and components thereof, the internal power transmitter 108, the control electrical circuitry 110, and the internal receiver 114 may be enclosed in the biocompatible protective packaging 132 that is at least partially transparent to the energy 112 output by the internal power transmitter 108. The biocompatible protective packaging 132 may be formed from a number of different biocompatible polymeric materials, such as at least one of polyxylene, polyethylene, poly(ethylene oxide), polyurethane, or poly(butylene terephthalate). The biocompatible protective packaging 132 may also be formed from a number of different biocompatible ceramics, such as silicate-based ceramics. In an embodiment, the biocompatible protective packaging 132 may be in the form of a biocompatible coating made from at least one of the aforementioned biocompatible polymeric or ceramic materials and formed over a relatively less biocompatible housing that provides structural support for the biocompatible coating or a housing formed from at least one of the aforementioned biocompatible materials.

Although the apparatus 102 includes the internal receiver 114 that may be disposed in the living subject 104, in other embodiments, the internal receiver 114 may be replaced with an external receiver that is external to the living subject 104. In such an embodiment, the external receiver may be in operable communication with the external device 118 or the control electrical circuitry 110. For example, the transmitter 120 of the external device 118 may transmit the one or more signals 116 encoding a request for information, which is received by the external receiver. For example, as opposed to the external device 118 directly sending the request to the internal receiver 114, the external receiver may communicate the request to a computer having a database that includes some or all of the requested information, which may be communicated to the external device 118 from the computer via a suitable wired or a wireless connection. In an embodiment, the computer may be in operable communication with, for example, the internal receiver 114 to provide a request for action or other instructions for controlling the operation of the internal power transmitter 108.

Figure 2:
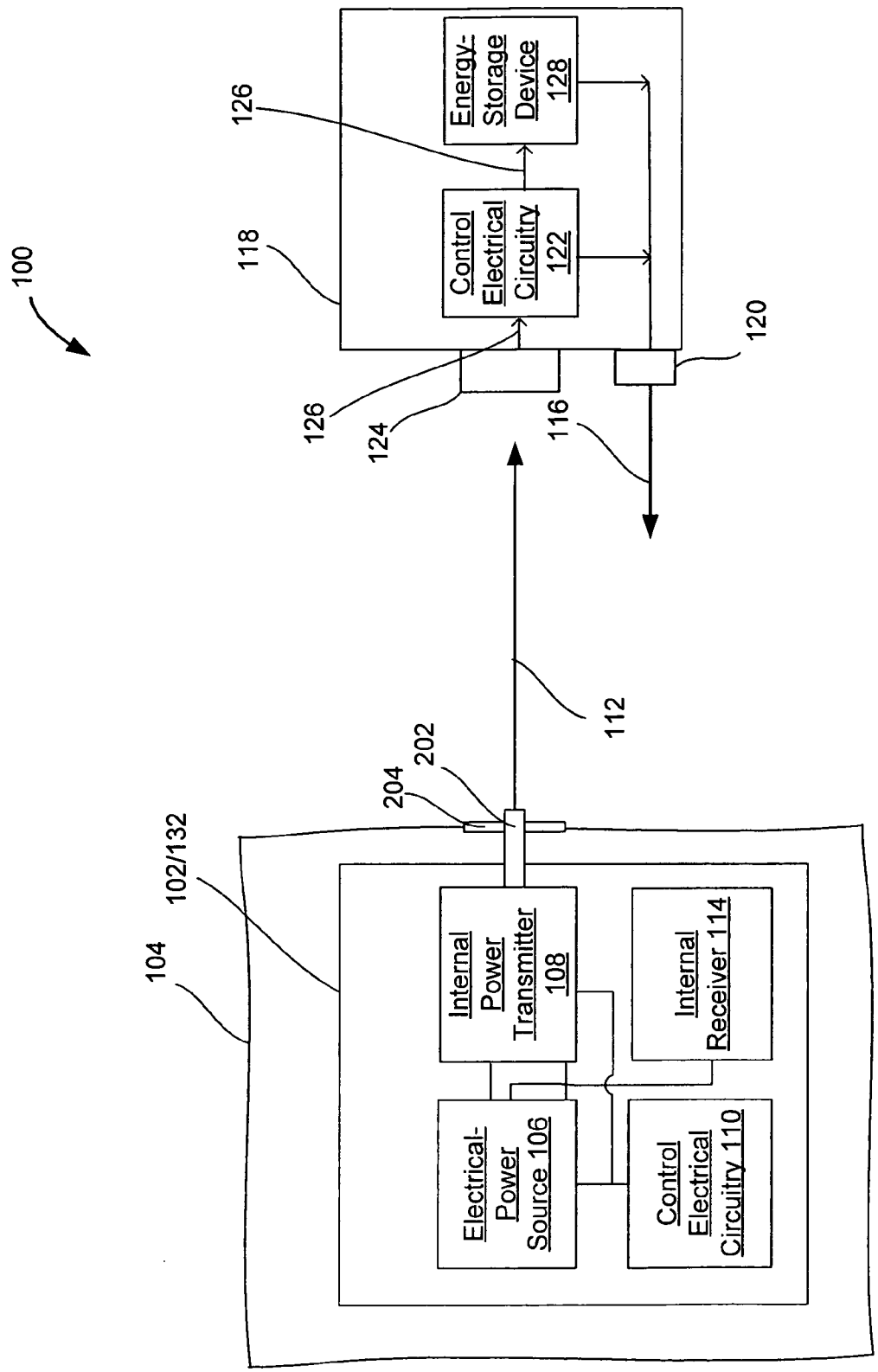
FIG. 2 is a functional block diagram of an embodiment of the system shown in FIGS. 1A and 1B in which optical waveguide is employed to deliver optical energy out of the living subject through an optical portal.

Referring to FIG. 2, in one or more embodiments, the energy 112 output by the internal power transmitter 108 may be delivered out of the living subject 104 through a portal. FIG. 2 is a functional block diagram of an embodiment of the system 100 in which optical power may be delivered through an optical portal formed in a living subject. In this embodiment, the internal power transmitter 108 is configured as an electrical-optical converter that outputs the energy 112 as one or more optical power signals. An optical waveguide 202 (e.g., one or more optical fibers) may be optically coupled to the electrical-optical converter to receive the energy 112 output therefrom and guide the energy 112 to a selected location in or out of the living subject 104. The optical waveguide 202 may extend out of the living subject 104 through a trocar housing 204 disposed in the living subject 104 that defines a portal therein.

In operation, the optical waveguide 202 may output the energy 112 as a beam that is received by the converter 124 (i.e., a power receiver) of the external device 118. In an embodiment, the optical waveguide 202 may be optically coupled to the converter 124 using a suitable optical connector structure or optical outlet received at least partially by the trocar housing 204. However, in an embodiment, the energy 112 may travel through free space to the converter 124 along with, optionally, being focused by one or more optical elements (e.g., one or more lenses) or directed to the converter 124.

Figure 3:
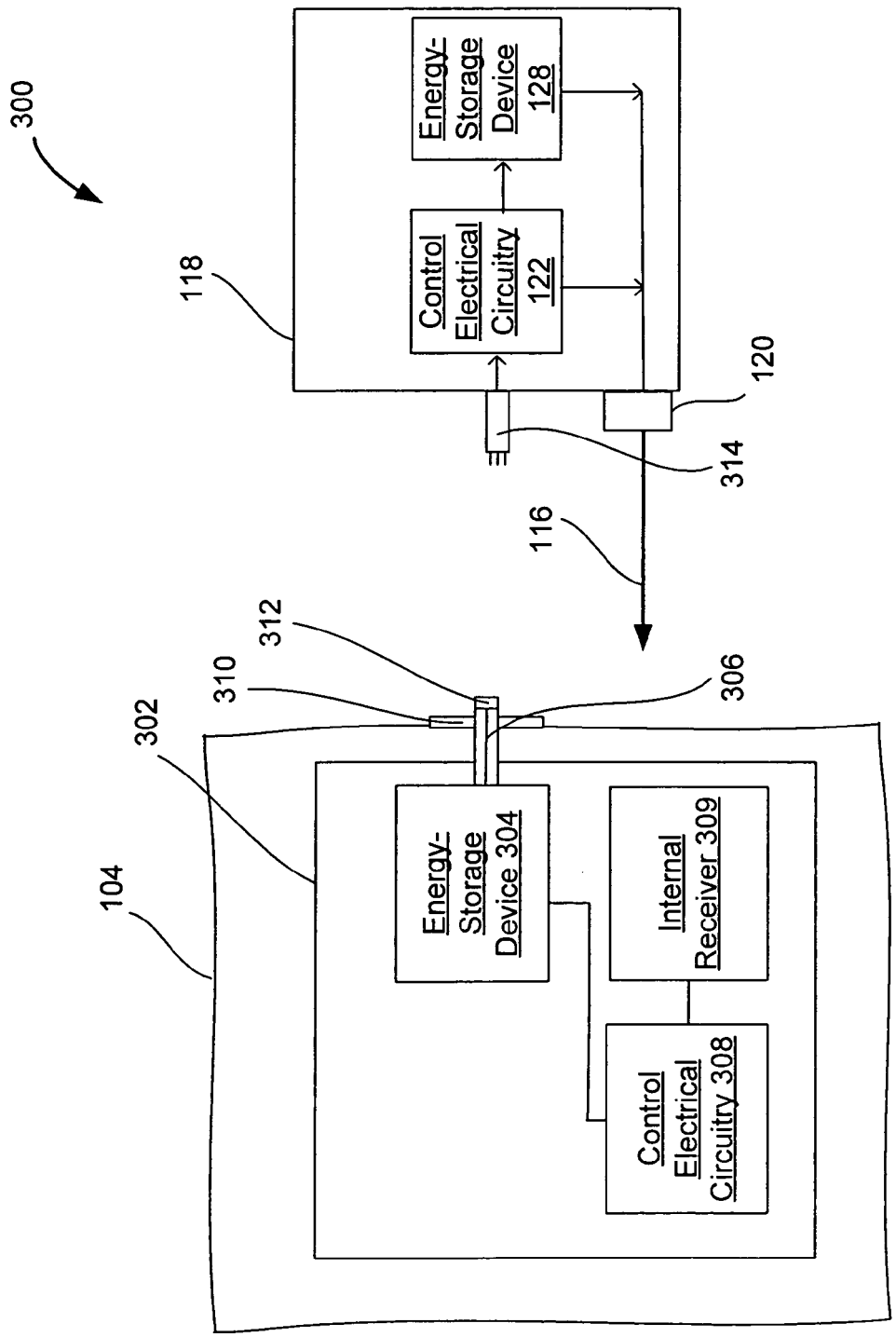
FIG. 3 is a functional block diagram of an embodiment of a system configured to deliver electrical power through an electrical outlet disposed in a living subject.

Referring to FIG. 3, in one or more embodiments, electrical energy may be delivered out of a living subject through a portal, such as an electrical outlet, to power at least one external device. FIG. 3 is a functional block diagram of an embodiment of a system 300 configured to deliver electrical power through an electrical outlet disposed in a living subject. In the system 300, an apparatus 302 includes an energy-storage device 304 (e.g., a battery or capacitive device) disposed in the living subject 104. The energy-storage device 304 is electrically coupled to one or more electrical conductors 306 (e.g., one or more electrical wires) that are suitably protected by a biocompatible sheath. The control of the distribution of electrical power from the energy-storage device 304 may be controlled by control electrical circuitry 308. The energy-storage device 304 and the control electrical circuitry 308, together, function as an internal power transmitter. An internal receiver 309 may be provided that is operably coupled to the control electrical circuitry 308 to instruct the control electrical circuitry 308 to control distribution of electrical power from the energy-storage device in accordance with the request for action encoded in the one or more signals 116 output by the external device 118. The one or more electrical conductors 306 may extend through a trocar housing 310 disposed in the living subject 104 that defines a portal therein. An electrical interface 312 (e.g., an electrical outlet) is electrically coupled to the one or more electrical conductors 306 and may be disposed in or project outwardly from the trocar housing 310 and the living subject 104. One or more electrical power signals may be transmitted from the energy-storage device 304, through the one or more electrical conductors 306, and to the electrical interface 312.

The external device 118 may further include an electrical interface/power receiver 314, such as (e.g., an electrical plug) configured to interface with the electrical interface 312 so that the stored electrical power can be delivered out of the living subject 104 to the energy-storage device 128 (e.g., a capacitive device or a battery) of the external device 118 under control of the control electrical circuitry 122.

Figure 4:
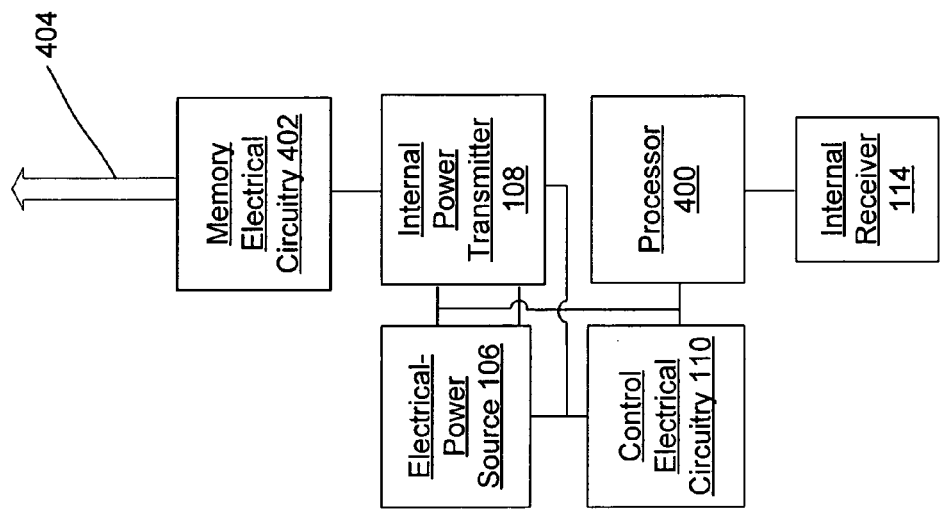
FIG. 4 is a functional block diagram of an embodiment for the apparatus shown in FIG. 1A that includes a processor configured to determine a response to a request for action from the external device and memory electrical circuitry configured to store information about the energy delivered by the apparatus.

FIG. 4 is a functional block diagram of an embodiment for the apparatus 102 shown in FIG. 1A that includes a processor 400 and memory electrical circuitry 402. The processor 200 is coupled to the internal receiver 114 to receive the request for action therefrom. The processor 400 is configured to determine a response to the request for action and instruct the control electrical circuitry 110 about how to control the operation of the internal power transmitter 108. The memory electrical circuitry 402 is coupled to the internal power transmitter 108. The memory electrical circuitry 402 stores information about various operational characteristics of the internal power transmitter 108. An output port 404 is coupled to the memory electrical circuitry 402 to enable downloading the information stored therein to another device, such as a desktop or handheld computer. For example, the memory electrical circuitry 402 may be coupled to the internal power transmitter 108 to store information about the energy 112 (see, for example, FIG. 1A) delivered by the internal power transmitter 108, such as power level of the energy 112, frequency of the energy 112, pulse duration of the energy 112, time profile of the energy 112, type of the energy 112, delivery characteristics of the energy 112, or other selected operational characteristic.

Figure 5A:
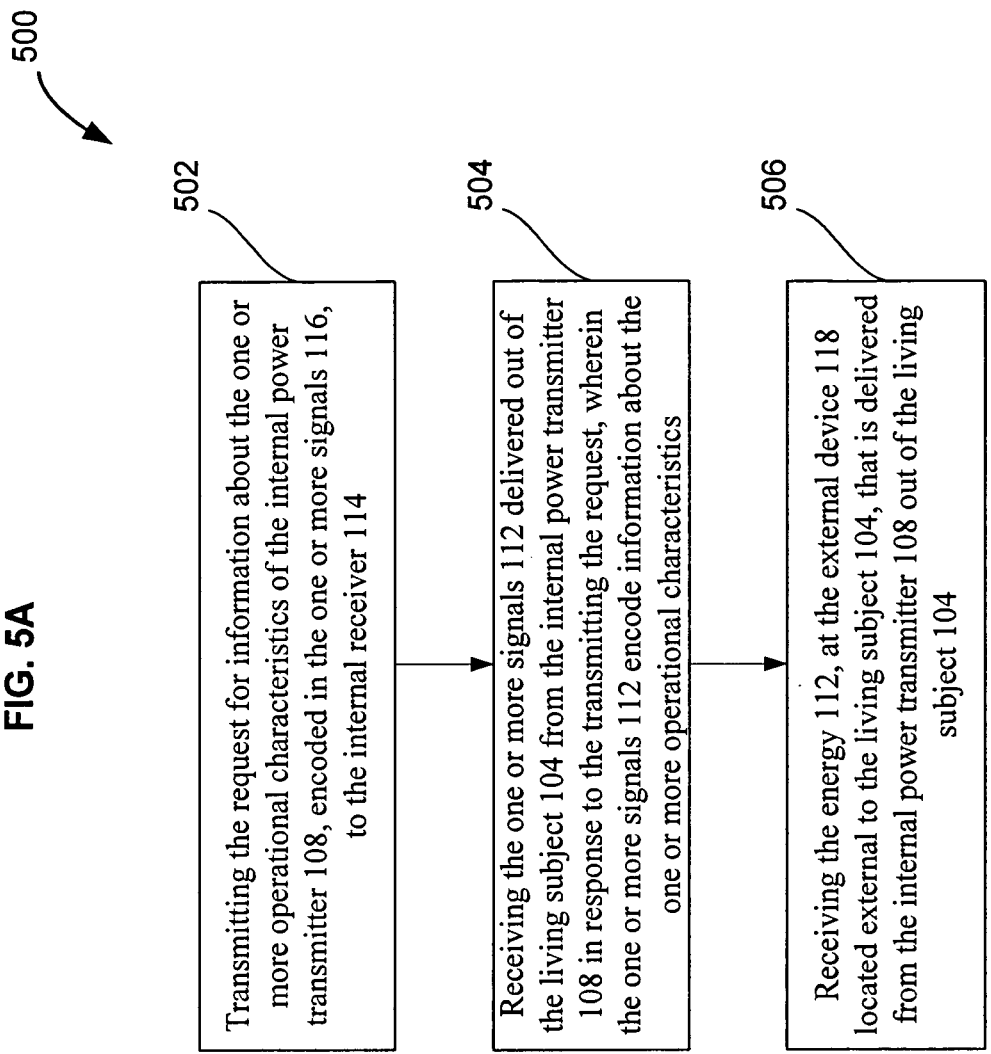
FIG. 5A is a flow diagram illustrating an embodiment of a method that may be implemented by any of the systems of FIGS. 1A-4.

FIGS. 5A-8 are flow diagrams that illustrate a number of embodiments of operational methods that may be implemented by the systems shown in FIGS. 1A-4. FIG. 5A is a flow diagram illustrating an embodiment of a method 500 that may be implemented by any of the systems of FIGS. 1A-4. For ease of description, the method 500 is described below with reference to the system 100 shown in FIG. 1A, and from the perspective of the external device 118. However, the method 500 may also be practiced using any of the embodiments shown in FIGS. 2-4.

The method 500 includes an act 502 of transmitting the request for information about one or more operational characteristics of the internal power transmitter 108, encoded in the one or more signals 116, to the internal receiver 114. The method 500 also includes an act 504 receiving the energy 112 in the form of one or more signals delivered out of the living subject 104 from the internal power transmitter 108 in response to the act 502. The one or more signals encode information about the requested one or more operational characteristics of the internal power transmitter 108. The method 500 further includes an act 506 of receiving the energy 112 (i.e., power), at the external device 118, that is delivered from the internal power transmitter 108 out of the living subject 104.

In an embodiment, the request for information in act 502 may be transmitted by the transmitter 120 transdermally through the tissue of the living subject 104 and to the internal receiver 114 as one or more optical or radio-frequency signals that encode the request. In an embodiment, the request for information in act 502 may be transmitted to the internal receiver 114 as one or more electrical data signals that encode the request.

Figure 5B:
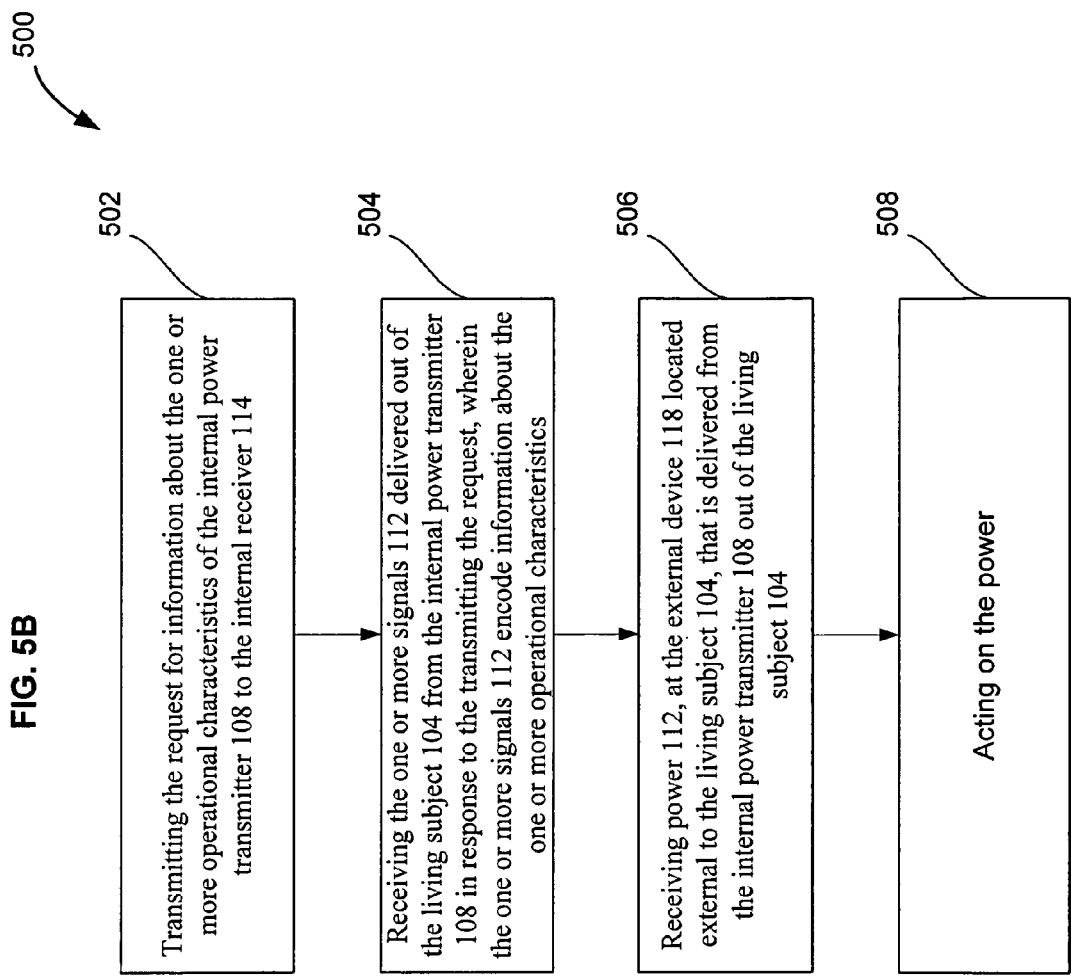
FIG. 5B is a flow diagram illustrating an embodiment of a method that may be implemented by any of the systems of FIGS. 1A-4.

Referring to FIG. 5B, in an embodiment, the method 500 further includes an act 508 of acting on the power 112 received by the external device 118. In an embodiment, the act 508 includes powering the external device 118 using energy at least associated with the power received by the external device 118. In an embodiment, the act 508 includes converting the power received by the external device 118 to the electrical power 126 using the converter 124. In an embodiment, the act 508 includes powering the external device 118 without converting the received energy 112, such as by delivering electrical energy as in the system 300 shown in FIG. 3. In an embodiment, the act 508 includes storing the power received by the external device 118 in, for example, the energy-storage device 128 of the external device 118. In an embodiment, the stored energy in the energy-storage device 128 may be delivered to another external device 118' via one or more power lines, or by removing and installing the energy-storage device 128 in the external device 118'.

Figure 6:
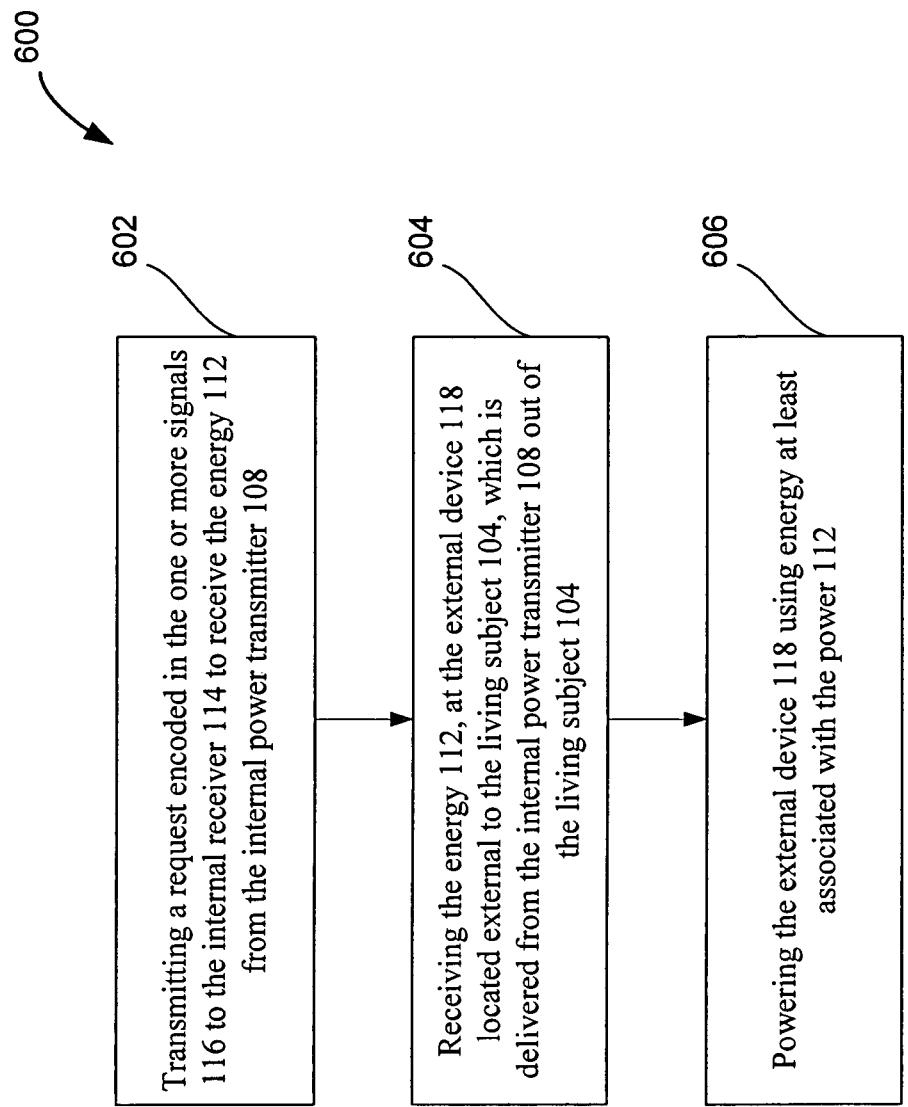
FIG. 6 is a flow diagram illustrating an embodiment of a method that may be implemented by any of the systems of FIGS. 1A-4.

FIG. 6 is a flow diagram illustrating an embodiment of a method 600 that may be implemented by any of the systems of FIGS. 1A-4. For ease of description, the method 600 is described below with reference to the system 100 shown in FIG. 1A, and from the perspective of the external device 118. However, the method 600 may also be practiced using any of the embodiments shown in FIGS. 2-4. The method 600 includes an act 602 of transmitting a request encoded in the one or more signals 116 to the internal receiver 114 to receive the energy 112 (i.e., power) from the internal power transmitter 108. For example, the one or more signals 116 may be transmitted by the transmitter 120 transdermally as one or more optical or radio-frequency signals or through a portal in the living subject 104. The method also includes an act 604 of receiving the energy 112, at the external device 118, which is delivered from the internal power transmitter 108 out of the living subject 104. The method further includes an act 606 of powering the external device 118 using energy at least associated with the power. For example, the converter 124 of the external device 118 may convert the received energy 112 to electrical energy or other form of energy as previously described. Further, the power may be delivered in the same form, such as one or more electrical signals as in the system 300 shown in FIG. 3.

In some embodiments, the method 600 includes sending a payment or payment authorization for the energy 112. The payment or payment authorization may be sent prior to or after the act 602.

In an embodiment, the method 600 further includes storing the energy 112 received by the external device 118 in, for example, the energy-storage device 128 of the external device 118. The stored energy in the energy-storage device 128 may be delivered to another external device 118' via one or more power lines, or by removing and installing the energy-storage device 128 in the external device 118'.

Figure 7:
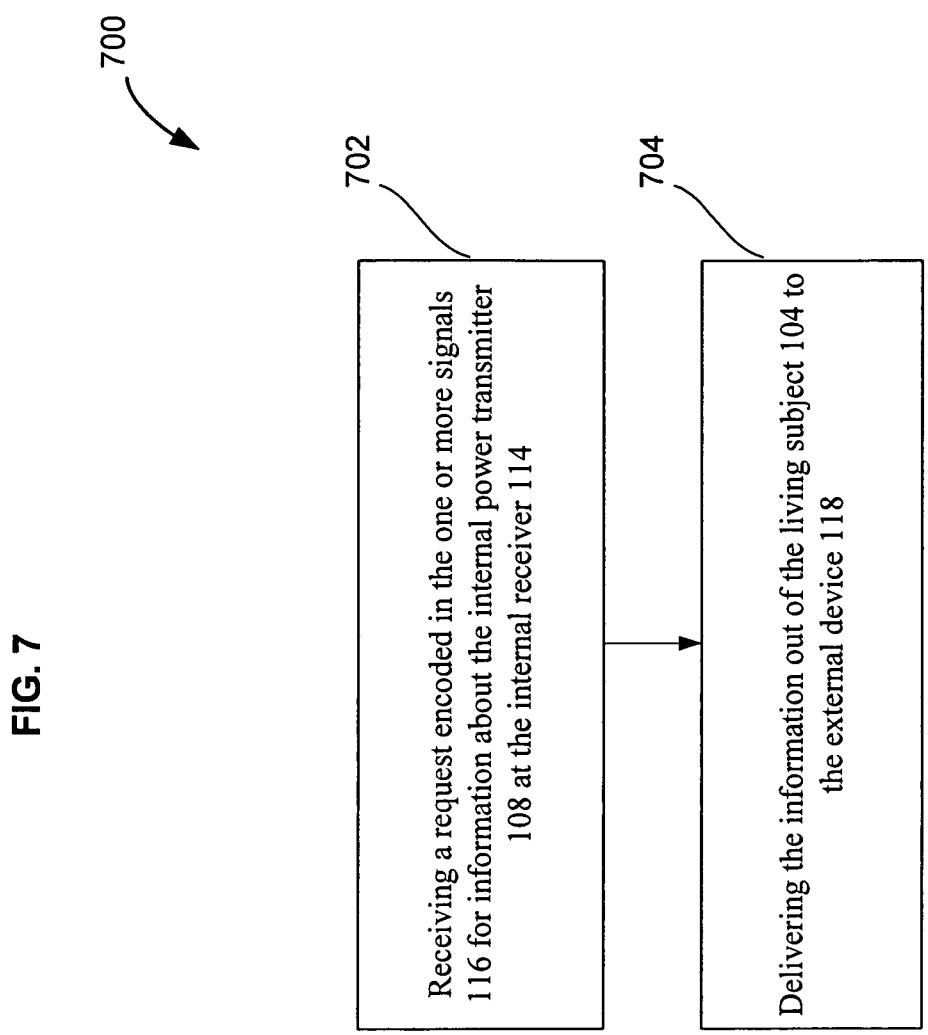
FIG. 7 is a flow diagram illustrating an embodiment of a method that may be implemented by any of the systems of FIGS. 1A-4.

FIG. 7 is a flow diagram illustrating an embodiment of a method 700 that may be implemented by any of the systems of FIGS. 1A-4. For ease of description, the method 700 is described below with reference to the system 100 shown in FIG. 1A, and from the perspective of the implanted apparatus 102 disposed in the living subject 104. However, the method 700 may also be practiced using any of the embodiments shown in FIGS. 2-4.

The method 700 includes an act 702 of receiving a request encoded in the one or more signals 116 for information about the internal power transmitter 108 at the internal receiver 114 associated with the internal power transmitter 108. For example, the one or more signals 116 may be received after being transmitted by the transmitter 120 transdermally as one or more optical, radio-frequency, ultrasonic, or electromagnetic signals or through a portal in the living subject 104. The method 700 further includes an act 704 of delivering the information out of the living subject 104 to the external device 118. For example, the energy 112 may be delivered from the internal power transmitter 108 to the external device 118 in response to receiving the request.

The information requested may include information about one or more operational characteristics exhibited by the internal power transmitter 108. For example, the one or more operational characteristics may include power level of the energy 112, frequency of the energy 112, pulse duration of the energy 112, time profile of the energy 112, type of the energy 112, delivery characteristics of the energy 112, price of the energy 112, location of the internal power transmitter 108, or amount of the available of the energy 112 available to be delivered by the internal power transmitter 108.

Figure 8:
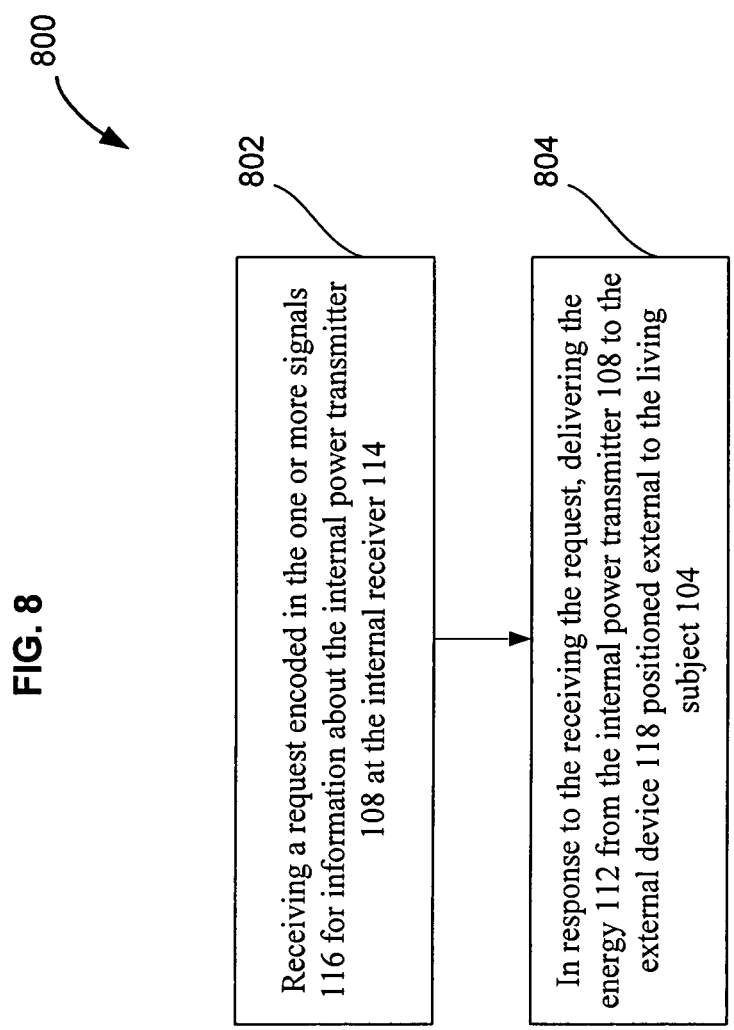
FIG. 8 is a flow diagram illustrating an embodiment of a method that may be implemented by any of the systems of FIGS. 1A-4.

FIG. 8 is a flow diagram illustrating an embodiment of a method 800 that may be implemented by any of the systems of FIGS. 1A-4. For ease of description, the method 800 is described below with reference to the system 100 shown in FIG. 1A, and from the perspective of the implanted apparatus 102 disposed in the living subject 104. However, the method 800 may also be practiced using any of the embodiments shown in FIGS. 2-4.

The method 800 includes an act 802 of receiving a request encoded in the one or more signals 116 for information about the internal power transmitter 108 at the internal receiver 114. For example, the one or more signals 116 may be received after being transmitted by the transmitter 120 transdermally through the living subject 104 or through a portal in the living subject 104. The information may include one or more operational characteristics of the internal power transmitter 108 previously described herein. The method 800 further includes an act 804 of delivering the energy 112 from the internal power transmitter 108 to the external device 118 in response to the act 802. For example, the energy 112 may be delivered transdermally out of the living subject 104 or through a portal in the living subject 104.

In an embodiment, the method 800 may further include delivering the energy 112 out of the living subject 104 having the information encoded therein. For example, the information may be delivered transdermally by the internal power transmitter 108 to the external device 118 and one or more operational characteristics of the external device 118 may be altered in response thereto.

Figure 9:
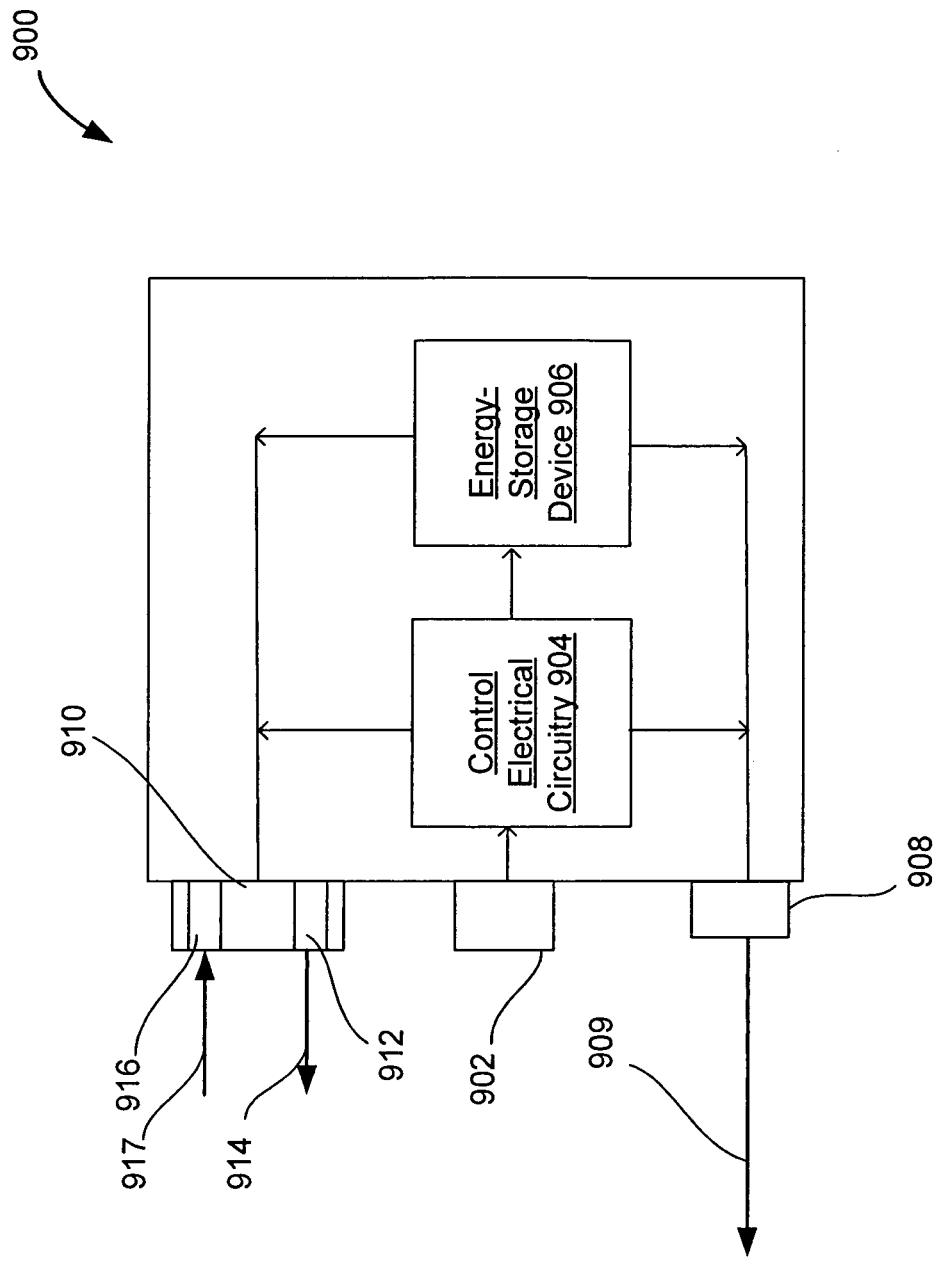
FIG. 9 is a functional block diagram of an embodiment of an external device suitable for use in any of the systems disclosed herein that is configured to coordinate a location thereof with respect to an internal power transmitter disposed in a living subject.

FIG. 9 is a functional block diagram of an embodiment of an external device 900 suitable for use in any of the systems disclosed herein that is configured to coordinate a location thereof with respect to an internal power transmitter disposed in a living subject. The external device 900 includes a power receiver 902 (e.g., any of the converters or electrical interfaces disclosed herein) coupled to control electrical circuitry 904. The power receiver 902 is configured to receiver power delivered out of a living subject by an internal power transmitter, such as the internal power transmitter 108 shown in FIG. 1A. The control electrical circuitry 904 receives the received power either directly or after being converted to another type of energy, and controls distribution of the power to an energy-storage device 906 (e.g., a battery or capacitive device).

The external device 900 further includes a transmitter 908 configured to deliver a request for action encoded in one or more signals 909 to an internal receiver (e.g., the internal receiver 114 in FIG. 1A or other dedicated transmitter) disposed in the living subject. The transmitter 908 is powered by the energy-storage device 906 and the operation thereof is controlled by the control electrical circuitry 904. As previously described, the request for action may include a request for information about one or more operational characteristics of the internal power transmitter, such as power level, frequency, pulse duration, time profile, type, price, delivery characteristics, or available amount of energy that the internal power transmitter is capable of delivering out of the living subject, or other selected operational characteristic. The request for action may also include a request or authorization for the internal power transmitter to deliver energy or to stop delivering energy out of the living subject.

The external device 900 additionally includes a location-identifying device 910 configured to coordinate a location thereof with respect to the internal power transmitter (e.g., the internal receiver 114 in FIG. 1A) disposed in the living subject. In the illustrated embodiment, the location-identifying device 910 includes an electromagnetic power source 912 configured to output one or more electromagnetic signals 914 (e.g., one or more electromagnetic beams) and an electromagnetic receiver 916 configured to detect when one or more returned electromagnetic signals 917 having a selected power level are received thereby in response to the electromagnetic power source 912 outputting the one or more electromagnetic signals 914. For example, the one or more electromagnetic signals 914 may include one or more optical or radio-frequency signals. The one or more electromagnetic signals 914 may reflect off of, for example, the biocompatible packaging 132 (see FIG. 1A) of the apparatus 102 (see FIG. 1A). When the reflected electromagnetic energy received by the electromagnetic receiver 916 is of a sufficient power level, it indicates that the apparatus 102 has been successfully targeted and the relative location of the internal power transmitter is sufficiently ascertained. In an embodiment, the transmitter 908 is configured to transmit the request for action in response to the signal power level measured by the location-identifying device 910 being at the sufficient power level.

In an embodiment, the one or more returned electromagnetic signals 917 may include one or more re-transmitted electromagnetic signals. For example, the internal transmitter (e.g., the internal power transmitter 108 shown in FIG. 1A) may re-transmit the one or more electromagnetic signals 914 when received by the internal receiver (e.g., the internal receiver 114 shown in FIG. 1A).

In an embodiment, the location-identifying device 910 may include a beacon configured to transmit location information to the internal receiver disposed in the living subject. In such an embodiment, the internal power transmitter (e.g., the internal power transmitter 108 shown in FIG. 1A) may target the external device 900 by appropriate beam steering that may be accomplished using refractive, reflective, or diffractive optics. In an embodiment, the location-identifying device 910 may include a camera configured to detect the presence of the apparatus 102 in the living subject. For example, the camera may include a thermal imager. In other embodiments, the location-identifying device 910 may include an ultrasonic or a radar imager configured to detect the presence of the apparatus 102 in the living subject.

The reader will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. The reader will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. The reader will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the reader will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, the various embodiments described herein can be implemented, individually and/or collectively, by various types of electro-mechanical systems having a wide range of electrical components such as hardware, software, firmware, or virtually any combination thereof; and a wide range of components that may impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will also appreciate that examples of electro-mechanical systems include but are not limited to a variety of consumer electronics systems, as well as other systems such as motorized transport systems, factory automation systems, security systems, and communication/computing systems. Those skilled in the art will recognize that electro-mechanical as used herein is not necessarily limited to a system that has both electrical and mechanical actuation except as context may dictate otherwise.

In a general sense, the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). The subject matter described herein may be implemented in an analog or digital fashion or some combination thereof.

The herein described components (e.g., steps), devices, and objects and the discussion accompanying them are used as examples for the sake of conceptual clarity. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, the reader can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

In some instances, one or more components may be referred to herein as "configured to." The reader will recognize that "configured to" can generally encompass active-state components and/or inactive-state components and/or standby-state components, etc. unless context requires otherwise.

In some instances, one or more components may be referred to herein as "configured to." The reader will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense the convention (e.g., "a system having at least one of A, B, or C" would include but not be limited to systems that have A alone, B alone, C alone, A and B together, A and C together, B and C together, and/or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

With respect to the appended claims, the recited operations therein may generally be performed in any order. Examples of such alternate orderings may include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

While various aspects and embodiments have been disclosed herein, the various aspects and embodiments disclosed herein are for purposes of illustration and are not intended to be limiting, with the true scope and spirit being indicated by the following claims.

The invention claimed is:

1. A method, comprising:
transmitting a request for information, about one or more operational characteristics of an internal power transmitter, to a receiver, wherein at least the internal power transmitter is disposed within a living subject;
receiving one or more signals delivered out of the living subject from the internal power transmitter in response to the transmitting the request, wherein the one or more signals encode information about the one or more operational characteristics;
receiving power, at an external device located external to the living subject, that is delivered from the internal power transmitter out of the living subject; and
powering the external device using energy at least associated with the power.

2. The method of claim 1, wherein powering the external device using energy at least associated with the power includes powering the external device using the energy.

3. The method of claim 1, wherein transmitting a request for information about one or more operational characteristics of an internal power transmitter to a receiver includes transmitting the request transdermally into the living subject and to the internal power transmitter.

4. The method of claim 1, wherein transmitting a request for information about one or more operational characteristics of an internal power transmitter to a receiver includes transmitting the request through a portal disposed in the living subject.

5. The method of claim 1, wherein the receiver includes an internal receiver that is disposed in the living subject.

6. The method of claim 1, wherein the power includes at least one of electromagnetic energy, electric energy, electromagnetic energy, radio-frequency energy, magnetic energy, ultrasonic energy, or thermal energy.

7. The method of claim 1, wherein the external device includes an electronic device.

8. The method of claim 7, wherein the electronic device includes at least one of a cell phone, a hearing aid, a digital camera, or a personal data assistant.

9. The method of claim 1, further comprising converting the power to one or more types of energy.

10. The method of claim 1, further comprising storing the power in the external device.

11. The method of claim 10, further comprising delivering the stored power to another external device located external to the living subject.

12. The method of claim 11, wherein delivering the stored power to another external device includes transmitting the stored power.

13. The method of claim 11, wherein delivering the stored power to another external device includes delivering the stored power in a removable battery.

14. The method of claim 1, further comprising transmitting one or more signals to the receiver authorizing the power to be delivered by the internal power transmitter.

15. The method of claim 1, further comprising locating the internal power transmitter prior to transmitting the request.

16. The method of claim 1, further comprising powering the internal power transmitter with an electrical-power source.

17. The method of claim 16, wherein the electrical-power source includes an electricity generator configured to convert internal body energy from the living subject into electricity that is provided to the internal power transmitter.

18. An apparatus configured for disposal in a living subject, comprising:
- an internal power transmitter configured to deliver energy out of the living subject, the energy configured to power an external device located external to the living subject;
- an internal receiver configured to receive and process a request for action from the external device; and
- a biocompatible protective packaging at least partially enclosing the internal power transmitter and the internal receiver.

19. The apparatus of claim 18, wherein the request for action includes a request for information about one or more operational characteristics of the internal power transmitter or a request for authorization for the internal power transmitter to deliver the energy.

20. The apparatus of claim 19, wherein the one or more operational characteristics include power level of the energy, frequency of the energy, pulse duration of the energy, time profile of the energy, type of the energy, delivery characteristics of the energy, price of the energy, location of the internal power transmitter, or amount of available energy for the internal power transmitter to deliver.

21. The apparatus of claim 18, wherein the request for action includes a request for the energy at a selected power level, a request for the energy with a selected time profile, a request for a selected amount of the energy, or a request for the energy at a specific price.

22. The apparatus of claim 18, wherein the request for action includes a request for the energy at a specific price.

23. The apparatus of claim 18, wherein the internal power transmitter is configured to transmit the energy transdermally out of the living subject.

24. The apparatus of claim 18, wherein the internal power transmitter is configured to transmit the energy as at least one of electrical, electromagnetic, radio-frequency, optical, ultrasonic, thermal, or magnetic energy.

25. The apparatus of claim 18, wherein the internal power transmitter is configured to transmit the energy through a portal in the living subject.

26. The apparatus of claim 18, further comprising a processor coupled to the internal receiver to receive the request for action therefrom and determine a response thereto.

27. The apparatus of claim 18, further comprising memory electrical circuitry coupled to the internal power transmitter, the memory electrical circuitry configured to store information about the energy delivered by the internal power transmitter.

28. The apparatus of claim 18, further comprising a location-identifying device configured to locate the internal power transmitter in the living subject.

29. The apparatus of claim 18, further comprising an electricity generator configured to convert internal body energy from the living subject into electricity that powers the internal power transmitter.

30. The apparatus of claim 18, wherein the biocompatible protective packaging includes a biocompatible protective coating.

31. The apparatus of claim 30, wherein the biocompatible protective coating includes at least one of a biocompatible polymer or biocompatible ceramic.

32. The apparatus of claim 31, wherein the biocompatible polymer includes at least one of polyxylene, polyethylene, poly(ethylene oxide), polyurethane, or poly(butylene terephthalate).

33. A method, comprising:
- transmitting a request for information, about one or more operational characteristics of an internal power transmitter, to a receiver, wherein at least the internal power transmitter is disposed within a living subject;
- receiving one or more signals delivered out of the living subject from the internal power transmitter in response to the transmitting the request, wherein the one or more signals encode information about the one or more operational characteristics;
- receiving power, at an external device located external to the living subject, that is delivered from the internal power transmitter out of the living subject;
- storing the power in the external device;
- delivery the stored power to another external device located external to the living subject, wherein delivering the stored power includes transmitting the stored power and delivering the stored power in a removable battery.

* * * * *

UNITED STATES PATENT AND TRADEMARK OFFICE
CERTIFICATE OF CORRECTION

PATENT NO. : 8,639,347 B2  Page 1 of 1
APPLICATION NO. : 12/658627
DATED : January 28, 2014
INVENTOR(S) : Hyde et al.

It is certified that error appears in the above-identified patent and that said Letters Patent is hereby corrected as shown below:

In the claims:

Column 20
Line 37, change "delivery" to --delivering--

Signed and Sealed this
Twelfth Day of August, 2014

Michelle K. Lee
*Deputy Director of the United States Patent and Trademark Office*